(12) United States Patent
Peters et al.

(10) Patent No.: US 6,576,641 B2
(45) Date of Patent: Jun. 10, 2003

(54) FUSED HETEROCYCLIC COMPOUNDS AND THEIR USE IN THE TREATMENT OF NEURODEGENERATIVE DISEASES

(75) Inventors: Dan Peters, Malmö (SE); Mette Grønborg, København (DK); Arne Møller, Sjællands Odde (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 09/875,019

(22) Filed: Jun. 7, 2001

(65) Prior Publication Data

US 2002/0013336 A1 Jan. 31, 2002

Related U.S. Application Data

(63) Continuation of application No. PCT/DK00/00012, filed on Jan. 31, 2000.

(30) Foreign Application Priority Data

Jan. 19, 1999 (DK) .......................................... 1999 00061

(51) Int. Cl.$^7$ ..................... A61K 31/435; C07D 471/04
(52) U.S. Cl. ...................................... 514/302; 546/115
(58) Field of Search ........................... 546/115; 514/302

(56) References Cited

U.S. PATENT DOCUMENTS

| | | | |
|---|---|---|---|
| 4,335,128 A | 6/1982 | Blanchard et al. | 514/301 |
| 4,661,498 A | 4/1987 | Wick et al. | 514/302 |
| 5,190,938 A | 3/1993 | Badorc et al. | 546/215 |

FOREIGN PATENT DOCUMENTS

| | | |
|---|---|---|
| EP | 0170549 | 2/1986 |
| EP | 0358558 | 3/1990 |
| EP | 0542411 | 5/1993 |
| WO | 9611201 | 4/1996 |

OTHER PUBLICATIONS

Nagai Y et al: Chem. Pharm. Bull., vol. 25, No. 8, 1977, pp. 1911–1922, XP002900992 p.1913, compounds XXIIIa and XXXa,b p. 1913 p. 1916, last paragraph.
Shunsaku Inoue et al: Journal of Heterocyclic Chemistry vol. 23., No. 1, 1986, pp. 233–240, XP0092900993 p. 233, compounds 1 and 2.
Paul A. Lapchak: Amgen Inc., Department of Neuroscience, vol. 7, No. 3, (1996).
Olle Lindvall: University hospital, vol.4, (1994) pp.752–757.
Jurgen Winkler et al: Department of NeUrosciences, vol. 2 (6) (1994) pp.465–478.
"Neurotropnic Factors Enter The Clinic" vol. 264 May 6, 1994 pp.772–774.
Peter A. Pechan et al: Regeneration and Transplantation, vol. 6, No. 47 Mar. 1995 pp. 669–672.

*Primary Examiner*—Bernard Dentz
(74) *Attorney, Agent, or Firm*—Birch, Stewart, Kolasch & Birch, LLP

(57) ABSTRACT

The present invention relates to certain fused heterocyclic compounds (I)

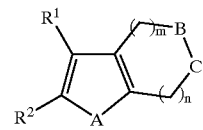

and their use in the treatment of neurodegenerative diseases and for the regeneration or prevention of degeneration of lesioned and damaged neurons.

7 Claims, 1 Drawing Sheet

FUSED HETEROCYCLIC COMPOUNDS AND THEIR USE IN THE TREATMENT OF NEURODEGENERATIVE DISEASES

This application is a Continuation of PCT International Application No. PCT/DK00/00012 filed on Jan. 31, 2000, which was published in English and which designated the United States and on which priority is claimed under 35 U.S.C. § 120, the entire contents of which are hereby incorporated by reference.

TECHNICAL FIELD

The present invention relates to certain fused heterocyclic compounds and their use in the treatment of neurodegenerative diseases and for the regeneration or prevention of degeneration of lesioned and damaged neurons.

BACKGROUND ART

Growth factors (or neurotrophic factors) promote the differentiation, growth and survival of numerous peripheral and central nervous system neurons during development and adulthood. The molecular characteristics, regulation and signal transduction mechanism for a number of neurotrophic factors have been identified. The most therapeutically promising of these molecules are nerve growth factor (NGF), brain-derived neurotrophic factor (BNDF), ciliary neurotrophic factor (CNTF), basic fibroblast growth factor (bFGF), insulin-like growth factor-I (IGF-I), and glial cell-line derived neurotrophic factor (GDNF).

Available data suggests that neurotrophic factors will be useful in the treatment of neurodegenerative diseases such as Alzheimer's disease, Parkinson's disease and amyotrophic lateral sclerosis. Additionally neurotrophic factors have shown beneficial effects in animal models of peripheral nerve damage and toxin induced neuropathy [*CNS Drugs* 1994 2 (6) 465–478].

Various rat studies predict that compounds mimicking or enhancing the function of NGF can rescue septal cholinergic neurons and alleviate benign forgetfulness and the memory impairment seen in senile dementia [*Science* 1994 264 772–774].

Recent studies have shown that NGF has a neuro protective effect on hippocampal neurons after cerebral ischaemia, which predicts a potential therapeutic role for NGF in the treatment of cerebral ischaemic neuronal damage [*NeuroReport* 1995 6 (4) 669–672].

Growth factors initiate their biological action by binding to specific cell surface receptors. Binding of the growth factor to its receptor activates the intracellular signal transduction, leading to the generation of various second messengers and activation of enzyme cascades, involving tyrosine kinases and protein kinase C, and culminates in a biological effect. The intracellular signal transduction pathway is not yet fully understood.

NGF and related neurotrophins are large peptides, which makes them unlikely therapeutic candidates. Poor pharmacokinetic parameters (e.g. poor oral absorption and short in vivo half life), and administration to the target organs represent the major problems.

There is a continued need for the development of new compounds capable of interacting with the neurotrophin-receptors, and which shows physicochemical properties different from the neurotrophins.

SUMMARY OF THE INVENTION

According to the present invention new neutrophically active compounds are provided. The neurotrophic activity has not been ascribed to a specific step in the interaction between NGF and its receptor or in the NGF signal transduction pathway.

The neurotrophic activity of the compounds of the invention makes them useful for the treatment or prevention of various degenerative diseases of the nerves, including Alzheimer's disease, Parkinson's disease, Huntington's disease, and amyotrophic lateral sclerosis (ALS), and for the alleviation of benign forgetfulness and the memory impairment seen in senile dementia or in connection with neurodegenerative diseases.

Moreover, the compounds of the invention have shown to be useful for the treatment of neuropathy and in particular peripheral neuropathy caused by e.g. genetic abnormalities and other conditions such as diabetes, polio, herpes and AIDS, and most especially neuropathy and peripheral neuropathy experienced by most cancer patients after or during chemotherapy.

The compounds of the present invention are considered to be particularly useful for the treatment of traumatic lesions of peripheral nerves, the medulla, and/or the spinal cord, and in the treatment of cerebral ischaemia, e.g. ischaemic neuronal damage following cardiac arrest, stroke, or postasphyxial brain damage in newborns, or following near-drowning.

In its first aspect the invention provides novel compounds characterized by the general formula (I)

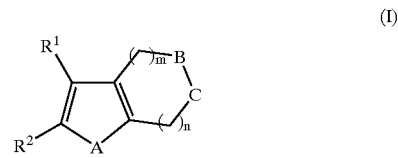

wherein n is 0 or 1;

m is 0 or 1;

A represents O, N—R' or S—R';

B represents O or N—R' or S—R' or CH—R';

C represents O or N—R" or S—R" or CH—R";

wherein R' and R" independently of each another represents hydrogen or a $C_{1-8}$-alkyl group, a $C_{2-8}$-alkenyl group, a $C_{2-8}$-alkynyl group, a $C_{3-8}$-cycloalkyl group, a $C_{3-8}$-cycloalkyl-$C_{1-8}$-alkyl group, which groups may be substituted one or more times with a substituent selected from the group consisting of hydroxy, $C_{1-8}$-alkyl, $C_{1-8}$-alkoxy, halogen, $NO_2$, CN, $NH_2$, $NH(C_{1-8}$-alkyl), and $N(C_{1-8}$-alkyl)$_2$;

or C represents an aralkyl group, which aryl group is optionally substituted one or more times with a substituent selected from the group consisting of hydroxy, $C_{1-8}$-alkyl, $C_{1-8}$-alkoxy, halogen, $NO_2$, CN, $NH_2$, $NH(C_{1-8}$-alkyl), and $N(C_{1-8}$-alkyl)$_2$;

$R^1$ and $R^2$ independently of each another represents hydrogen, a $C_{1-8}$-alkyl group, or a group of the formula $(CH_2)_k$-aryl, wherein k is 0, 1 or 2, and which aryl group may optionally be substituted one or more times with a substituent selected from the group consisting of hydroxy, $C_{1-8}$-alkyl $C_{1-8}$-alkoxy, halogen, $NO_2$, CN, $NH_2$, $NH(C_{1-8}$-alkyl), $N(C_{1-8}$-alkyl)$_2$, and $SO_2NR_3R_4$;

or $R^1$ and $R^2$ independently of each another represents a group of the formula $(CH_2)_k$-heteroaryl, wherein k is 0, 1 or 2, and which heteroaryl group may optionally be substituted one or more times with a substituent selected from the group consisting of hydroxy, C1-8-alkyl $C_{1-8}$-alkoxy, halogen, $NO_2$, CN, $NH_2$, $NH(C_{1-8}$-alkyl), $N(C_{1-8}$-alkyl$)_2$, and $SO_2NR_3R_4$:

wherein $R^3$ and $R^4$ independently of each another represents hydrogen or a $C_{1-8}$-alkyl group, or $R^3$ and $R^4$ together form a 5- to 8-membered ring which is partially or completely saturated;

or a pharmaceutically acceptable addition salt thereof.

In another aspect the invention provides a pharmaceutical composition comprising a therapeutically-effective amount of the compound of the invention, or a pharmaceutically acceptable salt thereof, together with at least one pharmaceutically acceptable carrier or diluent.

In a third aspect the invention relates to the use of a compound of the invention for the manufacture of a medicament for the treatment or alleviation or prevention of a disease or a disorder or a condition of a living animal body, including a human, which disease or disorder or condition is responsive to the activity of a neurotrophic agent.

In a fourth aspect the invention provides a method for treatment or alleviation or prevention of a disease or a disorder or a condition of a living animal body, including a human, which disease or disorder or condition is responsive to the activity of a neurotrophic agent, and which method comprises administering to such a living animal body, including a human, in need thereof a therapeutically effective amount of a compound of the invention.

Other objects of the invention will be apparent to the person skilled in the art from the following detailed description and examples.

DETAILED DISCLOSURE OF THE INVENTION
Novel Neutrophic Compounds

In its first aspect the invention provides novel chemical compounds of the general formula (I)

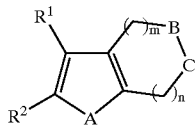

(I)

wherein n is 0 or 1;

m is 0 or 1;

A represents O, N—R' or S—R';

B represents O or N—R' or S—R' or CH—R';

C represents O or N—R" or S—R" or CH—R";

wherein R' and R" independently of each another represents hydrogen or a $C_{1-8}$-alkyl group, a $C_{2-8}$-alkenyl group, a $C_{2-8}$-alkynyl group, a $C_{3-8}$-cycloalkyl group, a $C_{3-8}$-cycloalkyl-$C_{1-8}$-alkyl group, which groups may be substituted one or more times with a substituent selected from the group consisting of hydroxy, $C_{1-8}$-alkyl, $C_{1-8}$-alkoxy, halogen, $NO_2$, CN, $NH_2$, $NH(C_{1-8}$-alkyl), and $N(C_{1-8}$-alkyl$)_2$;

or C represents an aralkyl group, which aryl group is optionally substituted one or more times with a substituent selected from the group consisting of hydroxy, $C_{1-8}$alkyl, $C_{1-8}$-alkoxy, halogen, $NO_2$, CN, $NH_2$, $NH(C_{1-8}$-alkyl), and $N(C_{1-8}$-alkyl$)_2$;

$R^1$ and $R^2$ independently of each another represents hydrogen, a $C_{1-8}$-alkyl group, or a group of the formula $(CH_2)_k$-aryl, wherein k is 0, 1 or 2, and which aryl group may optionally be substituted one or more times with a substituent selected from the group consisting of hydroxy, $C_{1-8}$-alkyl $C_{1-8}$-alkoxy, halogen, $NO_2$, CN, $NH_2$, $NH(C_{1-8}$-alkyl), $N(C_{1-8}$-alkyl$)_2$, and $SO_2NR_3R_4$;

or $R^1$ and $R^2$ independently of each another represents a group of the formula $(CH_2)_k$-heteroaryl, wherein k is 0, 1 or 2, and which heteroaryl group may optionally be substituted one or more times with a substituent selected from the group consisting of hydroxy, $C_{1-8}$-alkyl $C_{1-8}$-alkoxy, halogen, $NO_2$, CN, $NH_2$, $NH(C_{1-8}$-alkyl), $N(C_{1-8}$-alkyl$)_2$, and $SO_2NR_3R_4$;

wherein $R^3$ and $R^4$ independently of each another represents hydrogen or a $C_{1-8}$-alkyl group, or $R^3$ and $R^4$ together form a 5- to 8-membered ring which is partially or completely saturated;

or a pharmaceutically acceptable addition salt thereof.

In a preferred embodiment the compound of the invention is a compound of the general formula I, wherein both of n and m are 1.

In another preferred embodiment the compound of the invention is a compound of the general formula I, wherein A represents O.

In a third preferred embodiment the compound of the invention is a compound of the general formula I, wherein B represents N—R', and wherein R' represents hydrogen or a $C_{1-8}$-alkyl group, a $C_{2-8}$-alkenyl group, a $C_{2-8}$-alkynyl group, a $C_{3-8}$-cycloalkyl group, a $C_{3-8}$-cycloalkyl-$C_{1-8}$-alkyl group, which groups may be substituted one or more times with a substituent selected from the group consisting of hydroxy, $C_{1-8}$-alkyl, $C_{1-8}$-alkoxy, halogen, $NO_2$, CN, $NH_2$, $NH(C_{1-8}$-alkyl), and $N(C_{1-8}$-alkyl$)_2$.

In a fourth preferred embodiment the compound of the invention is a compound of the general formula I, wherein C represents CH—R', and wherein R' represents hydrogen or a $C_{1-8}$-alkyl group, a $C_{2-8}$-alkenyl group, a $C_{2-8}$-alkynyl group, a $C_{3-8}$-cycloalkyl group, a $C_{3-8}$-cycloalkyl-$C_{1-8}$-alkyl group, which groups may be substituted one or more times with a substituent selected from the group consisting of hydroxy, $C_{1-8}$-alkyl, $C_{1-8}$-alkoxy), halogen, $NO_2$, CN, $NH_2$, $NH(C_{1-8}$-alkyl), and $N(C_{1-8}$-alkyl$)_2$.

In a fifth preferred embodiment the compound of the invention is a compound of the general formula I, wherein R" is hydrogen and wherein R' represents a $C_{1-8}$-alkyl group.

In a sixth preferred embodiment the compound of the invention is a compound of the general formula II

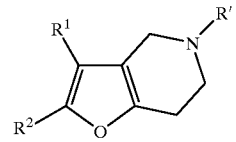

(II)

wherein R' represents hydrogen or a $C_{1-8}$-alkyl group, a $C_{2-8}$-alkenyl group, a $C_{2-8}$-alkynyl group, a $C_{3-8}$-cycloalkyl group, a $C_{3-8}$-cycloalkyl-$C_{1-8}$-alkyl group, which groups may be substituted one or more times with a substituent selected from the group consisting of hydroxy, $C_{1-8}$-alkyl, $C_{1-8}$-alkoxy, halogen, $NO_2$, CN, $NH_2$, $NH(C_{1-8}$-alkyl), and $N(C_{1-8}$-alkyl$)_2$;

$R^1$ and $R^2$ independently of each another represents hydrogen, a $C_{1-8}$-alkyl group, or a group of the formula $(CH_2)_k$-aryl, wherein k is 0, 1 or 2, and which aryl group may optionally be substituted one or more times with a substituent selected from the group consisting of hydroxy, $C_{1-8}$-alkyl $C_{1-8}$-alkoxy, halogen, $NO_2$, CN, $NH_2$, $NH(C_{1-8}$-alkyl), $N(C_{1-8}$-alkyl)$_2$, and $SO_2NR_3R_4$;

or $R^1$ and $R^2$ independently of each another represents a group of the formula $(CH_2)_k$-heteroaryl, wherein k is 0, 1 or 2, and which heteroaryl group may optionally be substituted one or more times with a substituent selected from the group consisting of hydroxy, $C_{1-8}$-alkyl $C_{1-8}$-alkoxy, halogen, $NO_2$, CN, $NH_2$, $NH(C_{1-8}$-alkyl), $N(C_{1-8}$-alkyl)$_2$, and $SO_2NR_3R_4$;

wherein $R^3$ and $R^4$ independently of each another represents hydrogen or a $C_{1-8}$-alkyl group, or $R^3$ and $R^4$ together form a 5- to 8-membered ring which is partially or completely saturated.

In a sixth preferred embodiment the compound of the invention is a compound of the general formula II wherein R' represents a $C_{1-8}$-alkyl group;

$R^1$ represents hydrogen or a phenyl group; and $R^2$ represents hydrogen, a benzyl group or a phenyl group, which groups may optionally be substituted one or two times in positions 3 and/or 4 with a substituent selected from the group consisting of hydroxy, halogen, $NO_2$, CN, $NH_2$, $NH(C_{1-8}$-alkyl), $N(C_{1-8}$-alkyl)$_2$, and $SO_2NR_3R_4$, wherein $R^3$ and $R^4$ independently of each another represents hydrogen or a $C_{1-8}$-alkyl group.

In its most preferred embodiment the compound of the invention is 6-(4-nitrophenyl)-furano[3,2-c]-N-butyl-1,2,3,4-tetrahydropyridine;

6-(4-aminophenyl)-furano[3,2-c]-N-butyl-1,2,3,4-tetrahydropyridine;

6-(3-nitrophenyl)-furano[3,2-c]-N-butyl-1,2,3,4-tetrahydropyridine;

6-(3-aminophenyl)-furano[3,2-c]-N-butyl-1,2,3,4-tetrahydropyridine;

7-phenyl-furano[3,2-c]-N-butyl-1,2,3,4-tetrahydropyridine; or furano[3,2-c]-N-hexyl-1,2,3,4-tetrahydropyridine;

or a pharmaceutically acceptable addition salt thereof.

Definition of Substituents

In the context of this invention halogen represents fluorine, chlorine, bromine, and iodine. Chlorine, bromine and iodine are the preferred halogens of this invention.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to eight carbon atoms ($C_{1-8}$-alkyl), including pentyl, isopentyl, neopentyl, tertiary pentyl, hexyl, isohexyl, heptyl and octyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), including at least one double bond. In a most preferred embodiment the alkenyl group of the invention is ethenyl; 1,2- or 2,3-propenyl; or 1,2-, 2,3-, or 3,4-butenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O-"group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention an imino group is an =N-alkyl group, in which the alkyl is as defined above.

In the context of this invention aryl designates a monocyclic or polycyclic aromatic hydrocarbon group. Examples of preferred aryl groups of the invention include phenyl, naphthyl and anthracenyl.

In the context of this invention an aralkyl group designates a mono- or polycyclic aryl group as defined above, which aryl group is attached to an alkyl group as also defined above. Examples of preferred aralkyl groups of the invention include benzyl, and phenethyl.

In the context of this invention the term heteroaryl designates a mono- or polycyclic aromatic compound, which holds one or more heteroatoms in its ring structure. Preferred heteroatoms include nitrogen (N), oxygen (O), and sulphur (S). Preferred heterocyclic monocyclic groups of the invention include 5- and 6 membered heterocyclic monocyclic groups.

Examples of preferred aromatic heterocyclic monocyclic groups of the invention include 1,3,2,4- or 1,3,4,5-dioxadiazolyl, dioxatniazinyl, dioxazinyl, 1,2,3-, 1,2,4-, 1,3,2- or 1,3,4-dioxazolyl, 1,3,2,4- or 1,3,4,5-dithiadiazolyl, dithiatriazinyl, dithiazinyl, 1,2,3-dithiazolyl, 2- or 3-furanyl, furazanyl, 1,2 or 4-imidazolyl, isoindazolyl, isothiazol-3,4 or 5-yl, isoxazol-3,4 or 5-yl, 1,2,3-, 1,2,4-, 1,2,5- or 1,3,4-oxadiazol-3,4 or 5-yl, oxatetrazinyl, oxatriazinyl, 1,2,3,4- or 1,2,3,5-oxatriazolyl, oxazol-2,4 or 5-yl, 2 or 3-pyrazinyl, 1,3 or 4-pyrazolyl, 3 or 4-pyridazinyl, 2,3 or 4-pyridinyl, 2,4 or 5-pyrimidinyl, 1,2 or 3-pyrrolyl (azolyl), 1,2,3,4- or 2,1,3,4-tetrazolyl, thiadiazol-3,4 or 5-yl, thiazol-2,4 or 5-yl, 2 or 3-thienyl, 1,2,3-, 1,2,4- or 1,3,5-triazinyl, and 1,2,3-, 1,2,4-, 2,1,3- or 4,1,2-triazolyl. Most preferred aromatic heterocyclic monocyclic groups of the invention are furan-2-yl, furan-3-yl, 2-, 4- or 5-imidazolyl, 3,4- or 5-isoxazolyl, 1-, 2- or 3-pyridinyl, and 1- or 2-thienyl.

Examples of preferred aromatic heterocyclic polycyclic groups of the invention include acridinyl, 2,4,5 or 6-benzimidazolyl, 1,2- or 1,4-benzisothiazinyl, 1,2- or 1,4-benzisoxazinyl, 1,3-benzisodiazolyl, benzothiazolyl, benzofuranyl, isobenzofuranyl, benzomorpholinyl, 2,3,4,5,6 or 7-benzofuranyl, 1,3,4,5,6 or 7-isobenzofuranyl, 1,2- or 1,4-benzopyranyl, 2,3-benzopyrronyl, 1,2,3,4-benzotetrazinyl, 1,3,4,6-benzotetrazolyl, 1,3,2-, 1,4,2-, 2,3,1- or 3,1,4-benzoxazinyl, 5 or 6-benzothiazolyl, 5 or 6-benzothienyl, 5 or 6-benzotrizolyl, 1,2,3- or 1,2,4- benzotriazinyl, 1,2,3- or 2,1,3-benzotriazolyl, benzoxadiazolyl, benzoxazolyl, carbazolyl, chromanyl, 4H-chromenyl, 6 or 7-cinnolinyl, coumarinyl, indanyl, 5 or 6-indazolyl, 2,3,4,5,6 or 7-indolyl, 1,3,4,5,6 or 7-isoindolyl, 5 or 6-indolizinyl, purinyl, phenazinyl, phenothiazinyl, phenanthridinyl, 1,4,5,6,7,8-phthalazinyl, pteridinyl, 2,3,4, 5,6,7 or 8-quinolinyl, 1,3,4,5,6,7 or 8-isoquinolinyl, 2,4,5, 6,7,8-quinazolinyl, 6 or 7-quinolinyl, 6 or 7-quinolizinyl, 2,3,5,6,7,8-quinoxalinyl, thieno[3.2-b]thienyl, thieno[2.3-b]thienyl, and xanthrenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or I- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Methods of Preparation

The compounds of the invention may be prepared by conventional methods for chemical synthesis, e.g. those described in the working examples. The starting materials for the processes described in the present application are known or may readily be prepared by conventional methods from commercially available chemicals.

The end products of the reactions described herein may be isolated by conventional techniques, e.g. by extraction, crystallisation, distillation, chromatography, etc.

Biological Activity

As demonstrated in the working examples, the compounds of the invention show neutrophic activity. The neurotrophic activity has not been ascribed to a specific step in the interaction between NGF and its receptor or in the NGF signal transduction pathway.

The neurotrophic activity of the compounds of the invention makes them useful for the treatment or prevention of various degenerative diseases of the nerves.

Moreover, the compounds of the invention have shown to be useful for the treatment of neuropathy and in particular peripheral neuropathy caused by e.g. genetic abnormalities and other conditions such as diabetes, polio, herpes and AIDS, and most especially neuropathy and peripheral neuropathy experienced by most cancer patients after or during chemotherapy.

The compounds of the present invention are considered to be particularly useful for the treatment of traumatic lesions of peripheral nerves, the medulla, and/or the spinal cord, and in the treatment of cerebral ischaemia, e.g. ischaemic neuronal damage following cardiac arrest, stroke, or postasphyxial brain damage in newborns, or following near-drowning.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefor, and, optionally, other therapeutic and/or prophylactic ingredients. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semi-permeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions which exhibit large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated and the route of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as $0.1\ \mu g/kg$ i.v. and $1\ \mu g/kg$ p.o. The upper limit of the dosage range is presently considered to be about 10 mg/kg i.v. and 100 mg/kg p.o. Preferred ranges are from about $0.1\ \mu g/kg$ to about 10 mg/kg/day i.v., and from about $1\ \mu g/kg$ to about 100 mg/kg/day p.o.

Methods of Therapy

In another aspect the invention provides a method for the treatment or alleviation of diseases or disorders or conditions of living animal bodies, including humans, which diseases, disorders or conditions is responsive to the activity of a neurotrophic agent, or to the activation or potentiation of nerve growth factors, and/or protein kinase C activation or potentiation and/or tyrosine kinase(s) activation or potentiation, and which method comprises administering to such a living animal body, including a human, in need thereof an effective amount of a chemical compound of the invention.

In a more preferred embodiment of the invention the diseases, disorders or conditions is caused by a traumatic lesion of peripheral nerves, the medulla, and/or the spinal cord.

In another preferred embodiment of the invention the diseases, disorders or conditions is a degenerative change, in particular dementia and memory impairment associated with dementia, caused by cerebral ischaemic neuronal damage, neuropathy and especially peripheral neuropathy, or Alzheimer's disease, Parkinson's disease, Huntington's disease, amyotrophic lateral sclerosis, or a neurodegenerative disease of the eye, including photoreceptor loss in the retina in patients afflicted with macular degeneration, retinitis pigmentosa, glaucoma, and similar diseases.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

BRIEF DESCRIPTION OF THE DRAWINGS

The present invention is further illustrated by reference to the accompanying drawing, in which:

FIG. 1 shows the protective effect of various concentrations [1 nM, 3 nM, 10 nM, 30 nM, 100 nM, 300 nM, $1\ \mu M$, $2\ \mu M$ and $10\ \mu M$, respectively] of a compound of the invention (Compound 1) on differentiated PC12 cells in serum free-medium;

EXAMPLES

Figure 1A:
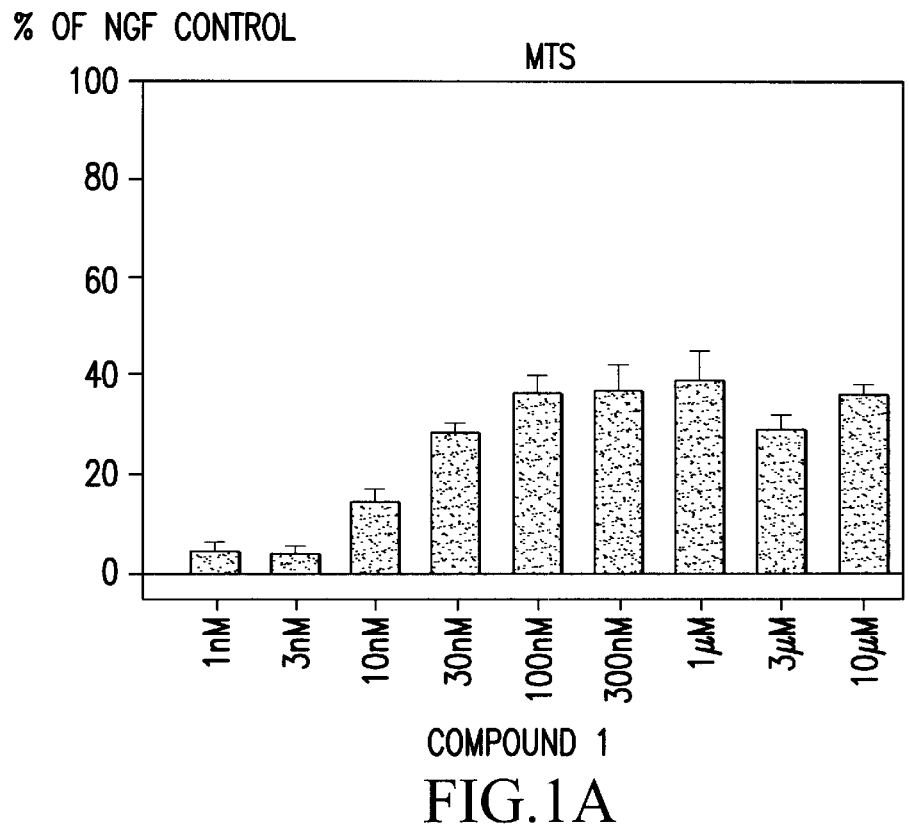
FIG. 1A shows the cell viability evaluated by reduction of MTS, which corresponds to the metabolic action of the cell culture [determined as a percentage of the NGF control]

The invention is further illustrated with reference to the following examples which are not intended to be in any way limiting to the scope of the invention as claimed.

Example 1

General:

All reactions involving air sensitive reagents or intermediates were performed under nitrogen and in anhydrous solvents. Magnesium sulphate was used as drying agent in the workup-procedures and solvents were evaporated under reduced pressure.

8-Butyl-1,4-dioxa-8-azaspiro[4,5]decane:

A mixture of 1,4-dioxa-8-azaspiro[4,5]decane (20.0 g, 140 mmol), 1-bromobutane (21,0 g, 154 mmol), potassium carbonate (19.3 g, 140 mmol) and dimethyl formamide (200 ml) was stirred for 5 h at 80° C. Sodium hydroxide (200 ml, 1 M) was added. The mixture was extracted three times with diethyl ether (200 ml). The product was isolated as an oil, in quantitative yield.

1-Butyl-4-piperidone:

A mixture of 8-butyl-1,4-dioxa-8-azaspiro[4,5]decane (27.8 g, 140 mmol) and hydrochloric acid (8 M, 350 ml) was refluxed for 15 h. The mixture was evaporated and sodium hydroxide (200 ml, 1 M) was added. The mixture was extracted twice with diethyl ether (150 ml). The crude product was purified by column chromaography using dichloromethane, methanol, aqueous ammonia (89:10:1). The pure product was isolated as an oil. Yield 10.5 g, 48%.

1-Butyl-4-(1-pyrolidinyl)-1,2,3,6-tetrahydropyridine:

A mixture of 1-butyl4-piperidone (10.5 g, 67.6 mmol), pyrrolidine (6.73 g, 94.7 mmol), amberlyst-15 (200 mg) and toluene (100 ml) was stirred at reflux overnight, with a Dean and Stark water collector connected. The crude mixture was co-evaporated with toluene twice (100 ml). The product was isolated as an oil in quantitative yield.

2-[3-(1-butyl-4-piperidonyl)]-p-nitroacetophenone:

To a mixture of 1-butyl-4-pyrolidinyl-1,2,3,6-tetrahydropyridine (8.0 g, 38.6 mmol) and toluene (100 ml) was added dropwise at room temperature, 2-bromo-p-nitroacetophenone (9.4 g, 38.6 mmol). The mixture was stirred overnight at room temperature. The crude mixture was evaporated and purified by column chromatography, using 4% methanol:dichloromethane as solvent. The product was isolated as an oil (2.54 g, 21%).

6-(4-Nitrophenyl)-furano[3,2-c]-N-butyl-1,2,3,4-tetrahydropyridine Fumaric Acid Salt (Compound 1):

A mixture of 2-[3-(1-butyl4-piperidonyl)]-p-nitroacetophenone (2.54 g, 8.0 mmol) and hydrochloric acid (25%, 25 ml) was stirred at reflux for 3 h. The mixture was evaporated and sodium hydroxide (1 M, 50 ml) was added followed by extraction six times with ethyl acetate (50 ml). The crude mixture was evaporated and purified by column chromatography, using 4% methanol:dichloromethane as solvent. The product was isolated as an oil. Yield 0.83 g, 35%. The corresponding salt was obtained by addition of a diethyl ether and methanol mixture (9:1) saturated with fumaric acid. Mp 94–98° C.

6-(4-Aminophenyl)-furano[3,2-c]-N-butyl-1,2,3,4-tetrahydropyridine Fumaric Acid Salt (Compound 2):

A mixture of 6-(4-nitrophenyl)-furano[3,2-c]-N-butyl-1,2,3,4-tetrahydropyridine (320 mg, 1.06 mmol), palladium on carbon (100 mg) and 20 ml ethanol was stirred under hydrogen for 5 h. The crude mixture was filtered and purified by chromatography, using petroleum 80–100° C. and ethyl acetate (1:1) as eluent. The corresponding salt was obtained by addition of a diethyl ether and methanol mixture (9:1) saturated with fumaric acid. Yield 240 mg, 59%.

2-[3-(1-Butyl-4-piperidonyl)]-m-nitroacetophenone:

To a mixture of 1-butyl4-pyrolidinyl-1,2,3,6-tetrahydropyridine (8.0 g, 38.6 mmol) and toluene (100 ml) was added dropwise at room temperature, 2-bromo-m-nitroacetophenone (9.4 g, 38.6 mmol). The mixture was stirred for two days at room temperature. The crude mixture was evaporated and purified with column chromatography, using 4% methanol:dichloromethane as solvent. The product was isolated as an oil. Yield 1.36 g, 11%.

6-(3-Nitrophenyl)-furano[3,2-c]-N-butyl-1,2,3,4-tetrahydropyridine Fumaric Acid Salt (Compound 3):

A mixture of 2-[3-(1-butyl4-piperidonyl)]-m-nitroacetophenone (1.3 g, 4.1 mmol) and hydrochloric acid (25%, 25 ml) was stirred at reflux for 10 h. The mixture was evaporated and sodium hydroxide (1 M, 50 ml) was added followed by extraction three times with ethyl acetate (30 ml). The crude mixture was evaporated and purified with column chromatography, using 4% methanol:dichloromethane as solvent. The product was isolated as an oil. Yield 0.59 g, 48%. The corresponding salt was obtained by addition of a diethyl ether and methanol mixture (9:1) saturated with fumaric acid. Mp 194–195° C.

6-(3-Aminophenyl)-furano[3,2-c]-N-butyl-1,2,3,4-tetrahydropyridine Fumaric Acid Salt (Compound 4):

A mixture of 6-(3-nitrophenyl)-furano[3,2-c]-N-butyl-1,2,3,4-tetrahydropyridine (230 mg, 0.77 mmol), palladium on carbon (100 mg) and 20 ml ethanol was stirred under hydrogen for 6 h. The crude mixture was filtered and purified by chromatography, using petroleum 80–100° C. and ethyl acetate (1:1) as eluent. The corresponding salt was obtained by addition of a diethyl ether and methanol mixture (9:1) saturated with fumaric acid. Mp 165–167° C. Yield 270 mg, 91%.

In a similar manner the following compounds were prepared: 7-phenyl-furano[3,2-c]-N-butyl-1,2,3,4-tetrahydropyridine; and furano[3,2-c]-N-hexyl-1,2,3,4-tetrahydropyridine.

Example 2

Survival of Differentiated PC12 Cells after NGF Withdrawal

This example demonstrates the neurotrophic effect of the compounds of the invention. Compound 1 prepared according to Ex. 1 and representative of the compounds of the invention was subjected to the following experiment.

PC12 cells are considered models for synaptic neurons for the investigation of neuronal differentiation and apoptosis.

PC12 cells were seeded in collagen coated 96 well plates at a cell density of $8000/cm^2$ in DMEM with 7.5% FCS, 7.5% HS and 2 nM NGF and cultured for 6 days.

The medium was then changed to DMEM without serum supplemented with the compound of the test compound in the concentrations indicated in FIG. 1. As a positive control, parallel wells receiving serum-free DMEM without addition of vehicle or 3 nM NGF were included.

After 4 days of incubation, cell viability was evaluated by reduction of MTS using the CellTiter 96 $AQ_{ueous}$ Non-radioactive Cell Proliferation Assay (available from Promega).

Data are expressed as % of the response seen with 3 nM NGF, and corrected for residual MTS reduction activity in the parallel serum-free cultures, cf. FIG. 1A.

In another assay cell viability after 4 days was evaluated by using the CyQUANT Cell Proliferation Kit from Molecular Probes. CyQUANT might give a better correlation with the actual cell number of the culture than MTS, which rather reflects the total metabolic activity of the culture, cf. FIG. 1B.

These experiments demonstrate that the compound of the invention shows a potent dose-dependent rescue of differentiated PC12 cells in serum-free medium at nanomolar concentrations (maximal protection at 100 nM).

Using MTS to measure cell viability, we see the maximal protection (approximately 30%) (FIG. 1A).

Figure 1B:
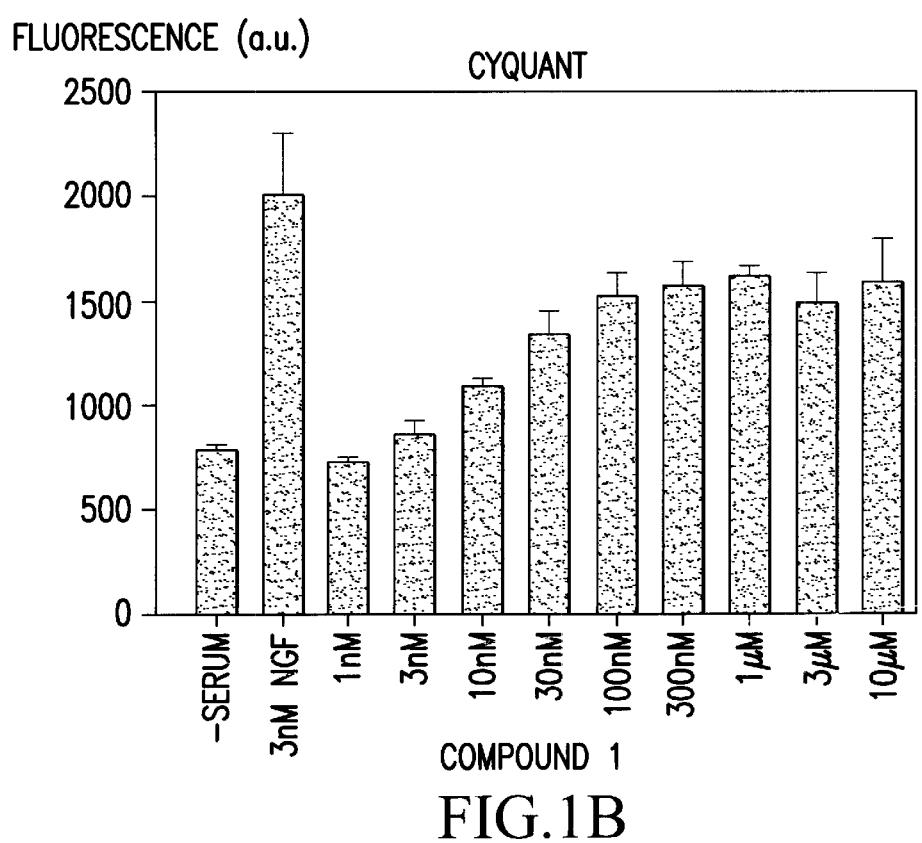
FIG. 1B shows the cell viability evaluated by CYQUANT, which is a measure of the amount of DNA and RNA in the culture [determined by fluorescence].

Using CyQUANT to evaluate cell survival a maximal rescue of approximately 50% is seen (FIG. 1B).

What is claimed is:

1. A compound having the formula (I)

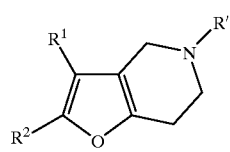

(II)

wherein

R' represents a $C_{3-8}$-alkyl group;

$R^1$ represents hydrogen or a phenyl group;

$R^2$ represents hydrogen, a benzyl group or a phenyl group, which groups may optionally be substituted one or two times in positions 3 and/or 4 with a substituent selected from the group consisting of hydroxy, halogen, $NO_2$, CN, $NH_2$, $NH(C_{1-8}$-alkyl), $N(C_{1-8}$-alkyl)$_2$, and $SO_2NR_3R_4$, wherein $R^3$ and $R^4$ independently of each another represents hydrogen or a $C_{1-8}$-alkyl group or a pharmaceutically acceptable addition salt thereof.

2. The compound of claim 1, said compound being 6-(4-nitrophenyl)-furano[3,2-c]-N-butyl-1,2,3,4-tetrahydropyridine;

6-(4-aminophenyl)-furano[3,2-c]-N-butyl-1,2,3,4-tetrahydropyridine;

6-(3-nitrophenyl)-furano[3,2-c]-N-butyl-1,2,3,4-tetrahydropyridine;

6-(3-aminophenyl)-furano[3,2-c]-N-butyl-1,2,3,4-tetrahydropyridine;

7-phenyl-furano[3,2-c]-N-butyl-1,2,3,4-tetrahydropyridine;

furano[3,2-c]-N-hexyl-1,2,3,4-tetrahydropyridine;

or a pharmaceutically acceptable addition salt thereof.

3. A pharmaceutical composition comprising a therapeutically-effective amount of a compound of claim 1, or a pharmaceutically acceptable salt thereof, together with at least one pharmaceutically acceptable carrier or diluent.

4. A method for treatment or alleviation or prevention of a disease or a disorder or a condition of a living animal body, including a human, which disease or disorder or condition is responsive to the activity of a neurotrophic agent, and which method comprises administering to such a living animal body, including said human, in need thereof a therapeutically effective amount of a compound of claim 1 or a pharmaceutically acceptable addition salt thereof.

5. The method of claim 4 wherein the disease or disorder or condition is responsive to the activation or potentiation of nerve growth factor(s).

6. The method of claim 4 for the treatment of a traumatic lesion of peripheral nerves, the medulla, the spinal cord, cerebral ischaemic neuronal damage, neuropathy, peripheral neuropathy, dementia, memory impairment caused by dementia, Alzheimer's disease, Huntingtons disease, Parkinson's disease, amyotrophic lateral sclerosis (ALS), or any other neurodegenerative disease or disorder or condition of a living animal body, including a human.

7. The method of claim 4 the prevention of the degenerative changes arising from cerebral ischaemic neuronal damage, neuropathy, peripheral neuropathy, dementia, Alzheimer's disease, Parkinson's disease, Huntington's disease, amyotrophic lateral sclerosis (ALS), or a neurodegenerative disease of the eye, including photoreceptor loss in the retina in patients afflicted with macular degeneration, retinitis pigmentosa, glaucoma, and similar diseases.

* * * * *

UNITED STATES PATENT AND TRADEMARK OFFICE
CERTIFICATE OF CORRECTION

PATENT NO. : 6,576,641 B2
DATED : June 10, 2003
INVENTOR(S) : Peters et al.

It is certified that error appears in the above-identified patent and that said Letters Patent is hereby corrected as shown below:

Title page,
Item [63], Related U.S. Application Data, should read -- Continuation of application No. PCT/D00/00012, filed on Jan. 13, 2000. --

Signed and Sealed this

Twenty-first Day of June, 2005

JON W. DUDAS
*Director of the United States Patent and Trademark Office*